US006492535B1

(12) United States Patent
Castiglioni et al.

(10) Patent No.: US 6,492,535 B1
(45) Date of Patent: Dec. 10, 2002

(54) PROCESS FOR THE PRODUCTION OF GAMMA-BUTYROLACTONE

(75) Inventors: Gian Luca Castiglioni, Riccione (IT); Carlo Fumagalli, Albano S. Alessandro (IT)

(73) Assignee: Lonza S.p.A., Milan (IT)

( * ) Notice: Subject to any disclaimer, the term of this patent is extended or adjusted under 35 U.S.C. 154(b) by 0 days.

(21) Appl. No.: 09/600,411

(22) PCT Filed: Jan. 19, 1999

(86) PCT No.: PCT/EP99/00336

§ 371 (c)(1),
(2), (4) Date: Jul. 17, 2000

(87) PCT Pub. No.: WO99/38856

PCT Pub. Date: Aug. 5, 1999

(30) Foreign Application Priority Data

Feb. 2, 1998 (IT) .......................................... MI98A0193

(51) Int. Cl.$^7$ ............................................. C07D 307/20
(52) U.S. Cl. ........................................................ 549/325
(58) Field of Search ............................................. 549/325

(56) References Cited

U.S. PATENT DOCUMENTS

| 3,065,243 A | 11/1962 | Dunlop et al. |
| 3,580,930 A | 5/1971 | Miya et al. |
| 4,083,809 A | 4/1978 | De Thomas et al. |
| 4,105,674 A | 8/1978 | De Thomas et al. |
| 5,347,021 A | 9/1994 | Taylor et al. |
| 5,637,735 A | 6/1997 | Tong et al. |

FOREIGN PATENT DOCUMENTS

| EP | 0322140 | 9/1989 |
| EP | 0 332 140 | 9/1989 |
| WO | WO 86/03189 | 6/1986 |
| WO | WO 86/07358 | 12/1986 |
| WO | WO 91/16132 | 10/1991 |

*Primary Examiner*—T. A. Solola
(74) *Attorney, Agent, or Firm*—Fisher, Christen & Sabol

(57) ABSTRACT

A process for the production of gamma-butyrolactone. Starting from maleic and/or succinic anhydride the conversion takes place in the vapor phase of a Cu/Cr catalyst.

15 Claims, No Drawings

PROCESS FOR THE PRODUCTION OF GAMMA-BUTYROLACTONE

BACKGROUND OF THE INVENTION

This application is a national stage application under 35 U.S.C. 371 of International Application (PCT) No. PCT/EP99/00336, filed on Jan. 19, 1999.

1. Field of the Invention

The present invention relates to a process for selective hydrogenation of maleic anhydride (MA) or succinic anhydride (SA) to gamma-butyrolactone (GBL) in the vapor phase using a catalyst comprising a mixed oxide of copper and chromium.

2. Background Art

GBL represents an example of small volume commodity of great industrial interest, because of its increasing demand. The main use of GBL is as intermediate for the synthesis of solvents with lower environmental impact than chlorinated ones, like pyrrolidone and N-methylpyrrolidone. It is also the raw material for the production of N-vinilpyrrolidone and of herbicides, pharmaceuticals and rubber additives. The first works on GBL synthesis appeared since 1940's, due to the start up of the Reppe process form acetylene and formaldehyde to give 1,4-butanediol (BDO) and then GBL by dehydrogenation. The draw-backs of this process are connected with the fluctuating prices of the raw materials and, mainly, with the hazard and the environmental impact of the use of both acetylene and formaldehyde.

During the second half of this century, other technologies have been studied and the number of patents about GBL production processes alternative to the Reppe process constantly increased.

The availability of maleic anhydride on industrial scale led to the development of new technologies for producing GBL, tetrahydrofurane (THF) or BDO by hydrogenation of maleic anhydride or of maleic anhydride derivatives like maleic acid diesters or succinic anhydride.

The liquid phase hydrogenation of MA to GBL has been employed in commercial production, but never reached great industrial importance.

Many patents describe the vapor phase hydrogenation of maleic anhydride or its esters, but mainly for the production of 1,4-butanediol; for instance WO 86/03189 describe the vapor phase hydrogenation of diethyl maleate to BDO.

WO 86/07358 describes a similar process for GBL production.

From a technological and economical point of view the esters of maleic acid or other maleic acid and/or succinic acid derivatives are less desirable raw materials compared with maleic anhydride.

Many patents describe the direct vapor phase hydrogenation of maleic anhydride to GBL, but none of them is completely satisfactory. Some of these patents claim the use of copper chromites as catalysts (e.g., U.S. Pat. No. 3,065, 243) but with unsatisfactory conversion and selectivity. Similar systems were claimed in U.S. Pat. No. 3,580.930 or in EP 332 140 (Cu/Zn/Cr/Al), but none of them is completely satisfactory in terms of GBL yield, productivity, by-products formation and catalyst durability.

The present invention provides a process for the vapor phase hydrogenation of maleic anhydride and/or succinic anhydride to GBL over a catalyst comprising a mixed oxide of copper and chromium.

The catalyst contains 30–80 wt % copper and 20–70 wt % chromium. Preferably the mixed oxide catalyst contains 35–55 wt % copper and 25–45 wt % Chromium. The catalyst may further contain the oxides of Barium and/or Manganese, the Barium or Manganese content thereby being less than 1 wt % chromium. The catalyst may further contain the oxides of barium and/or manganese, the barium or manganese content thereby being less than 1 wt %.

The catalyst composition may further contain inert components, such as, tabletting aids or inert fillers.

Preferred catalysts are commercially available, e.g., from Süd Chemie, Germany.

In the active state, the catalytically active oxide material may include some metallic components (e.g., metallic copper) formed in the activation step or during the hydrogenation.

The mixed oxide catalyst is subjected to an activation treatment comprising gradually increasing its temperature from room temperature to 200–380° C., preferably from 250–300° C., in the presence of a hydrogen-containing gas.

The hydrogen-containing gas in the activation treatment may be a mixture of hydrogen and nitrogen. After the activation treatment the catalyst is ready for use. Activation requires a time varying from 8–48 h, depending on reactor size and design.

The activation of the catalyst is exothermic. In case the reactor does not provide an efficient heat removal the hydrogen-containing gas must be suitably diluted or the space velocity must be increased to control exothermic peaks.

Hydrogen dilution results in longer time for the exothermic phase of activation. Large adiabatic reactors usually require the longest activation times. During operation molten maleic anhydride or succinic anhydride or a mixture thereof is expediently vaporized in a hot hydrogen stream in a mixing section in a mixing section; the mixture is then fed into the reactor packed with the above-described activated catalyst. Optionally the catalyst can be packed between two layers of an essentially inert support material, possibly with the same size and shape of the catalyst. Suitable examples of essentially inert support materials include silica, alumina, silica-alumina compound (e.g. mullite), silicon carbide, steatite and titania.

The reaction pressure is preferably between 1 and 100 bar, more preferably between 1 and 30 bar.

The molar ratio of hydrogen to anhydride in the feed is between 10:1 and 300:1 and more preferably between 40:1 and 230:1. Lower hydrogen to anhydride ratios result in tar formation and short catalyst life, higher ratios penalize the productivity of the catalyst.

The reaction temperature is preferably between about 150 and 350° C., and more preferably between 200 and 300° C.

As it is well known by those skilled in the art, temperature and pressure range in the hydrogenation reaction depend on the desired product mixture. Increasing temperature will result in the mix containing more THF, while increasing pressure will yield substantial amounts of BDO.

The following examples illustrate this invention in more detail.

EXAMPLE 1

Laboratory Scale Reactor 462 g of a commercial Cu/Cr catalyst, T-4466 from Süd Chemie AG (43 wt % Cu, 32.5 wt % Cr, <0.2 wt % Ba, <0.1% Mn) were packed in a 1 inch (2.54 cm) internal diameter tubular reactor; the resulting height of the bed was 0.7 m. The reactor was provided with an external jacket electrically heated to assure isotermicity all over the reactor length and with an axial thermowell with a movable thermocouple which was used to control and regulate the temperature in the catalyst bed.

The catalyst was activated in situ according to the following procedure: the temperature of the reactor was adjusted to 150° C. by means of the external jacket; a mixture of $H_2/N_2$ was passed over the catalyst. To avoid hot spots the activation was performed gradually: the hydrogen content was gradually increased from 0 up to 100% vol. and the temperature was risen to 250° C. During the procedure the bed temperature was checked by means of the axial thermocouple. The increase of temperature and hydrogen content was controlled in order not to exceed 25–30° C. as hot spot all along the catalytic bed. After 5 hours at 250° C. in hydrogen, the activation was stopped. After catalyst activation a mixture of hydrogen and maleic anhydride was fed to the catalyst bed at ambient pressure. Hydrogenation conditions and performances are summarised in table 1.

The MA conversion was complete all over the tests. The yield of GBL and of SA was constantly over 95% molar after the first 48 hours. SA can be recycled and fed back to the reactor.

TABLE 1

| T.O.S. | MA feed | $H_2$/MA | T | Molar Yield (%) | | | |
|---|---|---|---|---|---|---|---|
| (h) | (g/h) | (molar ratio) | (° C.) | GBL | SA | THF | Others |
| 29 | 11 | 180 | 231 | 82.0 | 16.4 | 0.2 | 1.4 |
| 53 | 12 | 171 | 230 | 86.5 | 12.0 | 0.2 | 1.3 |
| 95 | 12 | 165 | 231 | 75.7 | 22.5 | 0.0 | 1.8 |
| 142 | 12 | 162 | 237 | 87.5 | 9.7 | 0.3 | 2.5 |
| 182 | 14 | 137 | 243 | 89.6 | 8.0 | 0.1 | 2.3 |
| 205 | 13 | 156 | 249 | 93.2 | 2.2 | 0.4 | 4.2 |

GBL = γ-butyrolactone;
SA = succinic anhydride;
THF = tetrahydrofuran;
Others = mainly $C_2$–$C_4$ alcohols and acids.
T.O.S.: Time on Stream

EXAMPLE 2

Pilot Reactor

A tubular reactor with an internal diameter of 1 inch (2.54 cm) was packed with 2320 g of the same catalyst described in example 1; the resulting height of the bed was 3 m.

The rector was provided with an external jacket with a circulation of diathermic oil and was equipped with an axial thermowell and a movable thermocouple which was used to control and regulate the temperature in the catalyst bed.

The catalyst was activated in situ according to the following procedure: the temperature of the reactor was adjusted to 150° C. by means of the exteranal jacket; a mixture of $H_2/N_2$ was passed over the catalyst: the hydrogen content was gradually increased from 0 up to 5% vol. and the temperature was risen to 250° C. During the procedure the bed temperature was checked by means of the axial thermocouple. The increase of temperature and hydrogen content was controlled in order not to exceed 20–25° C. as hot spot all along the catalytic bed. After reaching 250° C. the hydrogen content in the gas stream was gradually increased up to 100%. After 5 hours at 250° C. in hydrogen, the activation was stopped.

After catalyst activation a mixture of hydrogen and maleic anhydride was fed to the catalyst bed at a pressure of 5 bar. Hydrogenation conditions and performances are summarised in table 2.

The MA conversion was complete all over the tests. The yield of GBL has constantly been in the range 94–96% molar.

TABLE 2

| T.O.S. | MA feed | $H_2$/MA | T | Molar Yield (%) | | | |
|---|---|---|---|---|---|---|---|
| (h) | (g/h) | (molar ratio) | (° C.) | GBL | SA | THF | Others |
| 8 | 163 | 129 | 237 | 92.8 | 5.6 | 0.6 | 1.0 |
| 67 | 174 | 120 | 247 | 94.6 | 1.0 | 1.2 | 3.2 |
| 150 | 160 | 127 | 247 | 95.8 | 2.1 | 0.6 | 1.5 |
| 219 | 184 | 95 | 252 | 96.0 | 1.4 | 0.6 | 2.0 |
| 279 | 198 | 100 | 254 | 95.0 | 1.6 | 0.7 | 2.7 |
| 399 | 235 | 101 | 256 | 95.5 | 2.0 | 0.6 | 1.9 |
| 445 | 210 | 98 | 258 | 96.8 | 0.0 | 0.7 | 2.5 |
| 592 | 225 | 70 | 266 | 94.2 | 1.9 | 0.7 | 3.2 |
| 660 | 216 | 77 | 272 | 92.4 | 2.8 | 0.8 | 4.0 |
| 776 | 172 | 97 | 272 | 94.9 | 0.7 | 0.9 | 3.5 |

GBL = γ-butyrolactone;
SA = succinic anhydride;
THF = tetrahydrofuran;
Others = mainly $C_2$–$C_4$ alcohols and acids.
T.O.S.: Time on Stream

What is claimed is:

1. A process for the production of gamma-butyrolactone comprising catalytically hydrogenating maleic anhydride and/or succinic anhydride in a vaporous mixture with hydrogen-containing gas in contact with a catalyst, said catalyst comprising a catalytically active oxide material and optionally an inert support, said catalytically active oxide material comprising a mixed oxide of copper and chromium, said mixed oxide having a content of copper of 30 to 80 weight percent and of chromium of 20 to 70 weight percent, said mixed oxide additionally containing the oxide of barium and/or manganese, the content of barium and/or manganese in said mixed oxide each being less than 1 weight percent.

2. The process according to claim 1, wherein said mixed oxide has a content of copper of 35 to 55 weight percent and of chromium of 25 to 45 weight percent.

3. The process according to claim 2, wherein said mixed oxide additionally contains the oxides of barium and manganese.

4. The process according to claim 3, wherein the molar ratio of hydrogen to anhydride in the vaporous mixture of the hydrogen-containing gas and the maleic anhydride and/or succinic anhydride is between 10 to 1 and 300 to 1.

5. The process according to claim 4, wherein the hydrogenation is conducted at a temperature between about 150 and 350° C.

6. The process according to claim 5, wherein the hydrogenation is conducted at a pressure of about 1 and 100 bar.

7. The process according to claim 6, wherein the anhydride is maleic anhydride.

8. The process according to claim 1, wherein the anhydride is maleic anhydride.

9. The process according to claim 2, wherein the anhydride is a mixture of maleic anhydride and succinic anhydride.

10. The process according to claim 2, wherein the anhydride is succinic anhydride.

11. The process according to claim 1, wherein the molar ratio of hydrogen to anhydride in the vaporous mixture of the hydrogen-containing gas and the maleic anhydride and/or succinic anhydride is between 10 to 1 and 300 to 1.

12. The process according to claim 1, wherein the hydrogenation is conducted at a temperature between about 150 and 350° C.

13. The process according to claim 1, wherein the hydrogenation is conducted at a pressure between about 1 and 100 bar.

14. The process according to 2, wherein the molar ratio of hydrogen to anhydride in the vaporous mixture of the hydrogen-containing gas and the maleic anhydride and/or succinic anhydride is between 10 to 1 and 300 to 1 the hydrogenation is conducted at a temperature of between about 150 and 350° C., and the hydrogenation is conducted at a pressure of about 1 to 100 bar.

15. The process according to claim 14, wherein the anhydride is maleic anhydride.

* * * * *